United States Patent [19]

Zavelovich et al.

[11] Patent Number: 4,643,812

[45] Date of Patent: Feb. 17, 1987

[54] PHOTOCHEMICAL PROCESS FOR THE HYDROBROMINATION OF OLEFINIC DOUBLE BONDS

[75] Inventors: Joshua Zavelovich, Lincolnwood; K. Virupaksha Reddy, Naperville, both of Ill.

[73] Assignee: Standard Oil Company (Indiana), Chicago, Ill.

[21] Appl. No.: 694,610

[22] Filed: Jan. 24, 1985

[51] Int. Cl.[4] .............................................. B01J 19/12
[52] U.S. Cl. ........................... 204/157.61; 204/157.94
[58] Field of Search ....... 204/158 HA, 163 R, 157.61, 204/157.94

[56] References Cited

U.S. PATENT DOCUMENTS 4,417,964 11/1983 Wolfrum et al. ................ 204/157.61

FOREIGN PATENT DOCUMENTS 825476 12/1959 United Kingdom ........... 204/157.94

Primary Examiner—Howard S. Williams
Attorney, Agent, or Firm—Richard A. Kretchmer; William T. McClain; William H. Magidson

[57] ABSTRACT

The free radical hydrobromination reaction of an olefinic compound is initiated photochemically by irradiating a mixture of hydrogen bromide and the olefinic compound with coherent light having a wavelength in the range from about 335 to about 500 nm.

15 Claims, 1 Drawing Figure

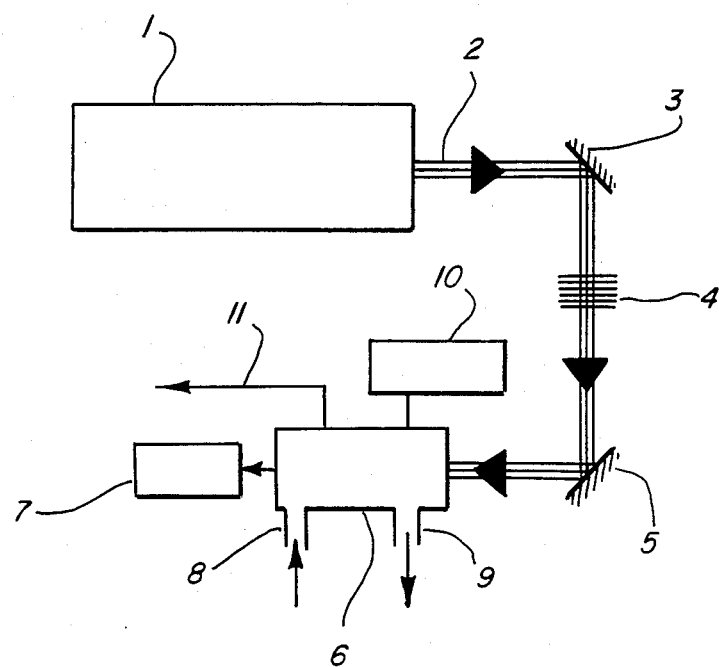

PHOTOCHEMICAL PROCESS FOR THE HYDROBROMINATION OF OLEFINIC DOUBLE BONDS

BACKGROUND OF THE INVENTION

1. Field of the Invention

This invention relates to a photochemical process for initiating the free radical reaction of hydrogen bromide with olefinic double bonds. More particularly, it relates to a photochemical process for initiating the hydrobromination of olefinic double bonds which involves a two-photon excitation of hydrogen bromide.

2. Description of the Prior Art

Free radical chain reactions are well-known processes which are of importance in the preparation of certain organic polymers from olefinic monomers, in the halogenation of alkanes, and in the hydrohalogenation of olefins. Typically, reactions of this type are initiated either by heating the reactants with an unstable radical precursor, such as a peroxide, or by photochemically generating appropriate free radicals in the presence of the reactants.

The free radical chain reaction of hydrogen bromide with olefins is a well-known process which can be initiated photochemically by irradiation of the reaction mixture with ultraviolet light having a wavelength shorter than about 300 nm. For the case of ethylene, this process can be described by the following equations:

$$HBr + h\nu \rightarrow H\cdot + Br\cdot \quad (1)$$

$$CH_2=CH_2 + Br\cdot \rightarrow \cdot CH_2CH_2Br \quad (2)$$

$$\cdot CH_2CH_2Br + HBr \rightarrow CH_3CH_2Br + Br\cdot \quad (3)$$

$$Br\cdot + \cdot CH_2CH_2Br \rightarrow CH_2BrCH_2Br \quad (4)$$

Equation 1 sets forth an initiation reaction which involves the photochemical conversion of a molecule of hydrogen bromide to a hydrogen atom (H.) and a bromine atom (Br.). This photochemical conversion is caused by a photon (hν) which has an energy in excess of the hydrogen bromide dissociation energy of 3.76 eV. Ethyl bromide is then produced by a free radical chain reaction, as set forth in Equations 2 and 3, which is initiated by the bromine atom formed according to equation 1. The bromine atom combines with an ethylene molecule to yield the .CH₂CH₂Br free radical (Equation 2) which, in turn, reacts with a molecule of hydrogen bromide to yield the ethyl bromide product and another bromine atom (Equation 3). The bromine atom produced according to Equation 3 then reacts with another molecule of ethylene according to Equation 2, and the propagation steps (Equations 2 and 3) continue to repeat until one of the free radical intermediates is destroyed in a termination reaction such as that illustrated by Equation 4.

The dissociation energy of hydrogen bromide is 3.76 eV. Accordingly, the initiation reaction (Equation 1) is carried out using photons having an energy which is equal to or in excess of this value. This consists of irradiating a reaction mixture of hydrogen bromide and an olefinic compound with light having a wavelength which is shorter than 330 nm (corresponding to an energy of 3.76 eV). In addition, the light must be of a wavelength which is absorbed by the hydrogen bromide. Since the light intensity from conventional lamp sources is extremely weak in the regions of the spectrum at which hydrogen bromide absorbs (i.e. at wavelengths shorter than 300 nm), the photochemical hydrobromination of olefins has been difficult to carry out efficiently using such sources. Alternatively, light having a wavelength shorter than 330 nm but longer than that at which hydrogen bromide absorbs can be utilized if the reaction mixture additionally contains a sensitizer such as acetone, benzophenone or acetophenone. This use of a sensitizer does not, however, involve a direct photolysis of hydrogen bromide. In addition, the use of sensitizers is not generally desirable since they result in the formation of undesirable byproducts.

U.S. Pat. No. 4,049,516, issued to Gellato et al. on Sept. 20, 1977, describes a conventional photochemical process for the hydrobromination of olefinic compounds. It is disclosed that hydrogen bromide absorbs light having a wavelength shorter than 300 nm and that the hydrobromination reaction can be initiated by direct photolysis of hydrogen bromide through the use of light having a wavelength which is not greater than 300 nm. In addition, it is disclosed that the hydrobromination reaction can be initiated indirectly with light of longer wavelength if a sensitizer such as benzophenone or acetophenone is incorporated into the reaction mixture. The photochemical addition of hydrogen bromide to 2-butene in the gas phase using a medium pressure mercury arc as a light source has been described in detail by G. A. Oldershaw et al., *J. Chem. Phys.*, Vol. 41, Dec. 1, 1964, pp. 3639–3644.

The commercial preparation of ethyl bromide by the hydrobromination of ethylene has been carried out photochemically using high energy ionizing radiation such as gamma radiation from a cobalt-60 radiation source. This process has been described in *Chemical Engineering Progress*, Vol. 60, April 1964, pp. 33–36 and also in U.S. Pat. No. 3,145,155, which issued to Pumpelly et al. on Aug. 18, 1964. Although this process has been commercially successful, it requires the use of extensive shielding and the use of a hazardous radiation source. In addition, the use of high energy ionizing radiation such as gamma radiation is undesirable because each photon carries about one million times the amount of energy actually required to dissociate a molecule of hydrogen bromide into atoms. This excess energy is converted into heat and results in an increase in the temperature of the reaction mixture, which is undesirable since the quantum yield of the reaction decreases as the temperature increases.

Mercury arc lamps are conventionally utilized as light sources for photochemical applications. However, U.S. Pat. No. 4,417,964, issued to Wolfrum et al. on Nov. 29, 1983, describes the use of a laser as a light source in a photochemical process for the preparation of olefinic compounds by splitting off hydrogen halide from the corresponding saturated compound. Similarly, a laser has been utilized as a light source in various photochemical isotope separation processes. For example, U.S. Pat. No. 4,025,408, issued to Marling on May 24, 1977, discloses a process for deuterium enrichment which involves the use of laser-produced infrared photons to induce the addition of a hydrogen halide to an olefin. More specifically, a mixture of a hydrogen halide feedstock and an unsaturated aliphatic compound is irradiated to selectively vibrationally excite those molecules of the hydrogen halide containing the desired isotope of hydrogen to a predetermined vibrational level. The excited molecules of hydrogen halide then preferentially react with the unsaturated aliphatic compound to form a product which is enriched in the desired isotope. This is not, however, a free radical process.

Unstable noble gas halides such as XeF, XeCl, XeBr, KrF and ArF have found use as light emitting species in lasers since they can be easily formed in excited states by electron-beam pumping or discharge pumping of suitable gas mixtures. Such lasers are referred to as excimer lasers. For example, a mixture of 10% xenon, 89% argon and 1% fluorine can be pumped with 400 keV electrons to produce excited XeF which emits light of 351 nm wavelength. Similarly, ArF, KrF and XeCl can be utilized to generate light of 193 nm, 248 nm and 308 nm, respectively.

Ethyl bromide, which can be manufactured by the hydrobromination of ethylene with hydrogen bromide, is a commercially significant material which has found use as a refrigerant, as an ethylating agent in organic synthesis, and as a grain and fruit fumigant.

SUMMARY OF THE INVENTION

The present invention is directed to the discovery that the free radical addition of hydrogen bromide to an olefinic double bond can be carried out photochemically in high quantum yield by irradiating the reaction mixture with coherent light having a wavelength in the range from about 335 to about 500 nm.

One embodiment of the invention is a method for the hydrobromination of an olefinic double bond in an organic compound which comprises irradiating a mixture of hydrogen bromide and said organic compound with coherent light of a wavelength in the range from about 335 to about 500 nm, wherein the intensity of said light is effective to initiate said hydrobromination reaction.

An object of this invention is to provide a photochemical method for the hydrobromination of olefinic double bonds which has a high quantum yield.

Another object of this invention is to provide a photochemical method for carrying out the free radical chain reaction of hydrogen bromide with an olefinic compound which uses light of a wavelength longer than 330 nm.

Another object of this invention is to provide a method for the initiation of the free radical hydrobromination of olefinic double bonds by the two-photon excitation of hydrogen bromide.

A still further object of this invention is to provide a photochemical method for the initiation of the free radical addition of hydrogen bromide to an olefinic double bond which does not involve the use of a sensitizer.

BRIEF DESCRIPTION OF THE DRAWING

The attached drawing is a schematic representation of the experimental apparatus which was utilized to evaluate the method of this invention.

DETAILED DESCRIPTION OF THE INVENTION

Although the single photon absorption of light by hydrogen bromide is negligible at wavelengths in the range from about 335 to about 500 nm, we have found that coherent light in this range of wavelengths can be utilized to initiate the free radical addition of hydrogen bromide to olefinic double bonds by dissociation of hydrogen bromide into its constituent atoms. The use of photons in this region of the spectrum would not be expected to initiate a free radical hydrobromination process in view of the low absorbance by hydrogen bromide in this region of the spectrum and the fact that these photons have an energy which is less than that which is required to dissociate the hydrogen bromide into its constituent atoms. We have found, however, that at these wavelengths, the very high photon concentrations produced by a laser cause the dissociation of hydrogen bromide by way of an unexpected multiple photon process. This multiple photon process can be utilized to initiate the free radical hydrobromination of olefinic double bonds in extremely high quantum yield. At 20° C. and using coherent light generated by an excimer laser which has a wavelength of 351 nm, we have found that the quantum yield for the photochemical free radical hydrobromination of ethylene is greater than 10,000, whereas the quantum yield for this reaction is only 0.06 and 400 at wavelengths of 193 and 248 nm, respectively.

Any olefinic compound having one or more olefinic double bonds can be used in the practice of this invention. Preferably, however, the olefinic compound is substantially transparent to the light which is employed. It will be appreciated, of course, that the olefinic compound can contain functional groups other than olefinic double bonds, which include but are not limited to hydroxyl and alkoxy groups. However, the process of this invention is desirably carried out with olefinic hydrocarbons and preferably with those olefinic hydrocarbons which contain unconjugated olefinic double bonds. Alkenes, which have only a single carbon-carbon double bond, are particularly satisfactory. Suitable olefinic compounds include, but are not limited to, ethylene, propylene, 1-butene, 2-butene, 2-methylpropene, 1-hexene, 1-octene, 1-decene, cyclohexene and 4-methyl-2-pentene.

The ratio of equivalents of olefinic compound to moles of hydrogen bromide in the process of this invention can be of any desired value. However, this ratio is desirably in the range from about 0.01 to about 100 and preferably about 10 to about 30. It will be appreciated, of course, that the equivalents of olefinic compound are calculated on the basis of the number of olefinic double bonds in this material. For example, with a compound that contains a single olefinic double bond, such as ethylene, the number of equivalents is equal to the number of moles. In contrast, with a compound which contains two olefinic double bonds, such as 1,9-decadiene, the number of equivalents is equal to twice the number of moles.

The photochemical hydrobromination of this invention does not require the use of a sensitizer. In addition, the reaction is desirably carried out either in the gas phase or the liquid phase and either in the presence or absence of a substantially inert diluent. When the olefinic compound is a gas at standard conditions, as is the case for ethylene and propylene, the process of this invention is conveniently carried out in the gas phase. Suitable diluents must be substantially inert under the conditions of the reaction and, additionally, should be substantially transparent to the light which is utilized to initiate the reaction. Suitable diluents include, for example, inert gases such as nitrogen and helium and organic solvents such as pentane, hexane, and cyclohexane.

The quantum yield for the free radical addition of hydrogen bromide to olefins ordinarily decreases with an increase in temperature. This is believed to be a result of the thermal instability of the intermediate organic free radical which is formed in the hydrobromination reaction. For the case of ethylene, this intermediate free radical is believed to decompose into ethylene and a bromine atom (the reverse of Equation 2) as shown in Equation 5.

$$\cdot CH_2CH_2Br \rightarrow CH_2 = CH_2 + Br \cdot \quad (5)$$

As the temperature increases, this decomposition competes more effectively with the propagation steps which are set forth above in Equations 2 and 3. Accordingly, the photochemical hydrobromination reaction of this invention is preferably carried out at relatively low temperatures. For example, the reaction is desirably carried out at a temperature below about 400° C., preferably below about 200° C., and more preferably below about 100° C.

Coherent light having a wavelength in the range from about 335 to about 500 nm is employed in the practice of this invention. Preferably, however, the wavelength is in the range from about 335 to about 400 nm. The source of the light is not critical, and any conventional laser can be utilized provided that the light produced by it is of sufficient intensity (provides a sufficient concentration of photons) to initiate the free radical chain reaction. For example, a laser producing pulsed radiation which is characterized by a pulse duration in the range from about 15 to about 30 nanoseconds and a pulse energy of about 50 to about 250 mJ is satisfactory for the practice of this invention. An excimer laser based on XeF and operating at 351 nm is particularly suitable.

The following examples are intended only to illustrate the invention and are not to be construed as imposing limitations on it.

EXAMPLE AND COMPARATIVE EXAMPLES

The drawing is a schematic representation of the apparatus which was utilized to illustrate the method of this invention. An excimer laser 1 was utilized to produce a coherent beam of light 2 which was reflected from a plane mirror 3 and passed through either a variable attenuator (in the case of 193 or 248 nm light) or a chlorine gas attenuation cell (in the case of 308 or 351 nm light) which is represented by 4 in the drawing. The resulting attenuated beam of light was then reflected from plane mirror 5, through reaction vessel 6, and into power meter 7 which was used to measure the energy of the light beam. Reactants were charged to reaction vessel 6 through inlet line 8 and reaction products were vented through exit line 9. The pressure within reaction vessel 6 was monitored with pressure gauge 10, and samples were removed from the reaction vessel for analysis by means of line 11. The excimer laser 1 was operated at 193 nm (ArF), 248 nm (KrF), 308 nm (XeCl) or 351 nm (XeF) by selection of an appropriate gas mixture and was characterized by pulse durations of 15-30 nanoseconds, a pulse energy of 50-250 mJ, and a repetition rate up to 100 Hz. The laser beam dimensions were approximately 0.5 cm×2.8 cm.

Two types of static reaction vessels were used. One was made of stainless steel with the inside walls Teflon-coated to avoid any metal catalysis. The other reaction vessel was constructed using a piece of Pyrex plumbing pipe which was 5.1 cm in diameter and 30 cm long. Suprasil windows (6.4 cm diameter and 0.8 cm thick) were mounted on the pipe ends with commercial clamps. A heating tape was wrapped around the reaction vessel to permit operation at elevated temperatures.

After a preset number of laser pulses, the resulting reaction mixture was analyzed by gas chromatography. Typically, a Porapak Q column (3 mm diameter and 2 m long) was used. In some cases, products were characterized by gas chromatography coupled with mass spectrometry. The laser was operated at 1 Hz or less repetition rate in order to allow for the completion of chain reactions from the previous laser pulse.

The results of a series of experiments involving the photoinitiation of the reaction between hydrogen bromide and ethylene using the above-described apparatus are summarized in Table I. In these experiments, a mixture of 30 Torr of hydrogen bromide with 700 Torr of ethylene was irradiated at 20° C. with a preset number of laser pulses ranging from 100 to 5,000. It will be seen from Table I that the absolute quantum yield ($\Phi$) changes by about five orders of magnitude from a value of 0.06 at 193 nm to a value which is greater than 10,000 at 351 nm.

Hydrogen bromide absorption cross-sections were determined at 248, 308 and 351 nm by measuring the transmittance of the laser beam through a sample cell filled with gaseous hydrogen bromide and are set forth in Table II. Path lengths and pressures were as follows: 21 cm and 58 Torr at 248 nm, 52 cm and 698 Torr at 308 nm, and 52 cm and 5,890 Torr at 351 nm. Absorbance at 308 nm and 351 nm was negligible; accordingly, the cross-section values determined at these wavelengths represent an upper limit. The other cross-section values set forth in Table II are derived from the literature.

TABLE I

Variation of Yield with Wavelength at 20° C.

| Laser | λ (nm) | Photon Energy (eV) | Yield[a] (E) | Quantum Yield ($\Phi$) |
|---|---|---|---|---|
| ArF | 193 | 6.42 | $I^{\frac{1}{2}}$ | 0.06 |
| KrF | 248 | 4.98 | [b] | 400 |
| XeCl | 308 | 4.03 | I | >3,500 |
| XeF | 351 | 3.53 | $I^2$ | >10,000 |

[a]Yield refers to the proportionality between the observed yield of ethyl bromide and the laser intensity I.
[b]At extremely low laser intensities, the yield increases with intensity. However, the yield becomes independent of intensity as the laser intensity increases.

TABLE II

Absorption Cross-Sections

| Laser | λ (nm) | $\sigma HBr^a$ (cm$^2$) | $\sigma Ethylene^b$ (cm$^2$) | Ethyl Bromide[b] (cm$^2$) |
|---|---|---|---|---|
| ArF | 193 | $1.8 \times 10^{-18}$ | $4.3 \times 10^{-20}$ | $4.8 \times 10^{-19}$ |
| KrF | 248 | $7.9 \times 10^{-21}$ | c | $1.5 \times 10^{-20}$ |
| XeCl | 308 | $<8.4 \times 10^{-24}$ | c | $3.8 \times 10^{-25}$ |
| XeF | 351 | $<1.0 \times 10^{-24}$ | c | c |

[a]Cross-section at 193 nm obtained from B. J. Hubert et al., J. Phys. Chem., 72, 3046 (1968).
[b]Numerical values obtained from Calvert et al., "Photochemistry" John Wiley & Sons, New York, N.Y., 1966.
[c]Regions of complete transparency.

Hydrogen bromide, ethylene and ethyl bromide all absorb strongly at 193 nm, and penetration depth in the reaction mixture by the 193 nm light was found to be 0.6 cm. This strong absorption at 193 nm leads to the creation of a large concentration of free radicals, and it is believed that chain termination is dominated by free radical recombinations as set forth in Equation 6.

$$H \cdot + Br \cdot \rightarrow HBr \quad (6)$$

Accordingly, the quantum yield is very low ($\Phi=0.06$) and the product yield varies with the square root of the laser pulse intensity. This type of behavior is typical of that observed for lamp initiated free radical chain reactions. Undesirable deposits were formed on the windows of the reaction vessel at this wavelength, apparently as a result of sequential photodissociation of molecular fragments by the intense short wavelength (193 nm) radiation.

At a wavelength of 248 nm, the quantum yield for the photoinitiated reaction of hydrogen bromide with ethylene was found to rise rapidly at very low laser intensities and become independent of intensity at higher intensities. The absolute quantum yield at 248 nm was found to be 400 at 20° C. However, the quantum yield was found to decrease to a value of 125 when the temperature of the reaction mixture was increased to 160° C., presumably as a result of the dissociation of the intermediate bromoethyl radical to bromine and ethylene (Equation 5). The reaction mixture is optically thin at 248 nm, and the penetration depth of the laser beam was 130 cm. Accordingly, the laser produced radical concentration is relatively low. At this wavelength, it is believed that the major chain termination step is diffusion of radicals to the walls of the reaction vessel. At 248 nm, the ethyl bromide product absorbs and appears to photodissociate. Even though the number of photochemically produced bromine atoms increases as the laser intensity increases, there also appears to be an increased destruction of the product ethyl bromide molecules. Accordingly, the product yield is independent of the laser pulse intensity.

At 308 nm, the absolute quantum yield for the photoinitated hydrobromination of ethylene was found to be about 3,500 at 20° C., and the hydrogen bromide absorption cross-section is less than $8.4 \times 10^{-24}$ cm$^2$. At this wavelength, the yield of ethyl bromide product varies linearly with the laser intensity. At 308 nm, it is believed that absorption and radical formation is a one-photon process and that the major termination process is the recombination of radicals at the walls of the reaction vessel.

At 351 nm, and in accordance with the process of this invention, the absolute quantum yield for the photoinitated hydrobromination of ethylene was found to be greater than 10,000 at 20° C., and the hydrogen bromide cross-section is less than $1.0 \times 10^{-24}$ cm$^2$. The product was pure ethyl bromide. At this wavelength, the yield of product is proportional to the square of the laser intensity. Any single photon process is ruled out because light of this wavelength consists of photons having an energy of 3.53 eV which is less than the hydrogen bromide dissociation energy of 3.76 eV. Only the absorption of two or more photons by hydrogen bromide can lead to its dissociation at 351 nm. There is no state of hydrogen bromide which can be resonant with 351 nm photons. Accordingly, it is believed that the photoinitiation of the hydrobromination of ethylene at this wavelength is by the simultaneous absorption of two photons by a molecule of hydrogen bromide. The sum of the energy of two of the 351 nm photons corresponds to the maximum of a one photon absorption band of hydrogen bromide in the vacuum ultraviolet.

We claim:

1. A method for the hydrobromination of an olefinic double bond in an organic compound which comprises irradiating a mixture of hydrogen bromide and said organic compound with coherent light of a wavelength in the range from about 335 to about 500 nm, wherein said organic compound is an alkene and the intensity of said light is effective to initiate said hydrobromination reaction.

2. The method as set forth in claim 1 wherein said coherent light has a wavelength in the range from about 335 to about 400 nm.

3. The method as set forth in claim 2 wherein the organic compound is substantially transparent to said light.

4. The method as set forth in claim 3 wherein said organic compound is ethylene.

5. The method as set forth in claim 3 wherein said coherent light has a wavelength of about 351 nm.

6. The method as set forth in claim 3 wherein said mixture is irradiated at a temperature which is below about 200° C.

7. The method as set forth in claim 6 wherein said mixture is irradiated at a temperature which is below about 100° C.

8. The method as set forth in claim 3 wherein said coherent light is pulsed with a pulse duration of about 15 to about 30 nanoseconds and a pulse energy of about 50 to about 250 mJ.

9. The method as set forth in claim 8, wherein the pulse repetition rate is about 1 Hz or less.

10. The method as set forth in claim 3 wherein said coherent light is produced by an excimer laser.

11. The method as set forth in claim 3 wherein the ratio of equivalents of olefinic compound to moles of hydrogen bromide is from about 0.01 to about 100.

12. The method as set forth in claim 3 wherein the mixture of said hydrogen bromide and said organic compound is in the gas phase.

13. The method as set forth in claim 3 wherein the mixture of said hydrogen bromide and said organic compound is in the liquid phase and additionally comprises a substantially inert diluent.

14. The method as set forth in claim 3 wherein said irradiation is carried out in the absence of a sensitizer.

15. The method as set forth in claim 3 wherein said alkene has only a single carbon-carbon double bond.

* * * * *